United States Patent
Swartz

(10) Patent No.: US 6,365,618 B1
(45) Date of Patent: Apr. 2, 2002

(54) ADMINISTRATION OF CARVEDILOL TO MITIGATE TARDIVE MOVEMENT DISORDERS, PSYCHOSIS, MANIA, AND DEPRESSION

(76) Inventor: Conrad M. Swartz, 3416 Quail Chase, Springfield, IL (US) 62707

( * ) Notice: Subject to any disclaimer, the term of this patent is extended or adjusted under 35 U.S.C. 154(b) by 0 days.

(21) Appl. No.: 09/737,290
(22) Filed: Dec. 13, 2000
(51) Int. Cl.$^7$ ............................................. A61K 31/40
(52) U.S. Cl. ...................................................... 514/411
(58) Field of Search ........................................ 514/411

(56) References Cited

U.S. PATENT DOCUMENTS 5,952,389 A * 9/1999 Fogel ........................... 514/665
6,071,966 A * 6/2000 Gold et al. ................... 514/579

OTHER PUBLICATIONS

Ban Ta et al., Nimodipine in the Treatment of Old Age Dementias, Prog Neuropsychopharmacol Biol Psychiatry, 1990, 14(4); pp. 525–551, (Abstract).
Yoram Barak et al., Vitamin E (α–Tocopherol) in the Treatment of Tardive Dyskinesia: A Statistical Meta–Analysis, Annals of Clinical Psychiatry, vol. 10, No. 3; 1998, pp. 101–105.
N. Biary et al., The Effect of Nimodipine on Essential Tremor, Neurology, 45(8); Aug. 1995, pp. 1523–1525, (Abstract).
Daniel B. Campbell et al., L–Type Calcium Channels Contribute to the Tottering Mouse Dystonic Episodes, The American Society for Pharmacology and Experimental Therapeutics, Molecular Pharmacology, 55; 1999, pp. 23–3.
Casey DE, Behavioral Effects of Sertindole, Risperidone, Clozapine and Haloperidol in Cebus Monkeys, Psychopharmacology, 124(1–2); Mar. 1996, pp. 134–140, (Abstract).
J Cheng et al., Carvedilol Blocks the Repolarizing K+ Currents and the L–type Ca2+ Current in Rabbit Ventricular Myocytes, Eur Journal Pharmacology, 376(1–2); Jul. 1999, pp. 189–201, (Abstract).
Guy Chouinard et al, Neuroleptic–Induced Supersensitivity Psychosis, Am Journal of Psychiatry, 135:11; Nov. 1978, pp. 1409–1410.
Cleland JG, Carvedilol for Heart Failure; More than Just a Beta–blocker?, Br J Hosp. Med., 9:58(10); Nov. 19— Dec. 9, 1998, pp. 493–497, (Abstract).
Cohn JN et al., Safety and Efficacy of Carvedilol in Severe Heart Failure. The U.S. Carvedilol Heart Failure Study Group, J Card Fail, 3(3); Sep. 1997, pp. 173–179, (Abstract).
Di Lenarda A et al., Long–term Effect of Carvedilol in Idiopathic Dilated Cardiomyopathy with Persistent Left Ventricular Dysfunction Despite Chronic Metoprolol. The Heart–muscle Disease Study Group, J Am Coll Cardiol, 33(7); Jun. 1999, pp. 1926–1934, (Abstract).
Michael F. Egan et al., The Treatment of Tardive Dyskinesia, Schizophrenia Bulletin, 23(4); 1997, pp. 583–609.

William M. Glazer, Review of Incidence Studies of Tardive Dyskinesia with Typical Antipsychotics, The Journal of Clinical Psychiatry Audiograph Series, vol. 2, No. 10; Aug. 1999, pp. 2–16.
Glazer WM et al., Predicting the Long–Term Risk of Tardive Dyskinesia in Outpatients Maintained on Neuroleptic Medications, Journal Clinical. Psychiatry, 54(4); Apr. 1993, pp. 133–139, (Abstract).
Hayashi T et al., Life–Threatening Dysphagia Following Prolonged Neuroleptic Therapy, Clinical. Neuropharmacology, 20(1); Feb. 1997, pp. 77–81, (Abstract).
Heintz R et al, Pargyline Reduces/Prevents Neuroleptic–Induced Acute Dystonia in Monkeys, Psychopharmacology (Berl), 93(2); 1987, pp. 207–213 (Abstract).
Hunt N. et al., Tardive Dyskinesia in Bipolar Affective Disorder: A Catchment Area Study, Int. Clinical. Psychopharmacology, 6(1); 1991, pp. 45–50, (Abstract).
Kang My et al., In Vitro Study on Antioxidant Potential of Various Drugs Used in the Perioperative Period, Acta Anaesthesiol Scand, 42(1); Jan. 1998, pp. 4–12, (Abstract).
Khan R et al., Speech Abnormalities in Tardive Dyskinesia, Am Journal Psychiatry, 151(5); May 1994, pp. 760–762, (Abstract).
Kobayashi T et al., Ca2+ Channel Antagonists and Neuroprotection from Cerebral Ischemia, Eur Journal Pharmacology, 363(1); Dec. 11, 1998, pp. 1–15, (Abstract).
Lieberman JA et al., The Effects of Clozapine on Tardive Dyskinesia, Br Journal Psychiatry, 158; Apr. 1991, pp. 503–510, (Abstract).
Maeda K et al., Severe Antecollis During Antipsychotics Treatment: A Report of Three Cases, Prog. Neuropsychopharmacol Biol Psychiatry, 22(5); Jul. 1998, pp. 749–759, (Abstract).
McLeod JR Jr., et al., Neurotoxicity Mediated by Aberrant Patterns of Synaptic Activity Between Rat Hippocampal Neurons in Culture, J Neurophysiol, 80(5); Nov. 1998, pp. 2688–2698, (Abstract).

(List continued on next page.)

Primary Examiner—Marianne C. Seidel
Assistant Examiner—Brian-yong Kwon

(57) ABSTRACT

The compound carvedilol has the chemical formula: ñ-1-(carbazol-4-yloxy)-3-[[2-(o-methyoxyphenoxy)ethyl]amino]-2-propanol. It exists in the form of optical isomers R- and S-carvedilol, and as mixtures of these isomers. It, or one of its optical isomers, is administered, preferably orally, several times per day in tablets of 3–25 mg for the treatment, prevention and clinical arrest of movement disorders associated with medications which block dopamine receptors, including many antipsychotic and antiemetic medications. Such movement disorders include tardive dyskinesia, tardive dystonia, and tardive akathisia. The compound carvedilol is also administered to improve the treatment of mental disorders in which dopamine-blocking medications are used, such as manic episodes, major depressive episodes, and psychoses such as schizophrenia and schizoaffective disorder.

3 Claims, No Drawings

OTHER PUBLICATIONS

Robert Miller et al., Loss of Straital Cholinergic Neurons as a Basis for Tardive and L–Dopa–Induced Dyskinesias, Neuroleptic–Induced Supersensitivity Psychosis and Refractory Schizophrenia, Biol Psychiatry, 34; 1993, pp. 713–738, Society of Biological Psychiatry.

Najib J. Tardive Dyskinesia: A Review and Current Treatment Options, Am J Ther, 6(1); Jan. 1999, pp. 51–60, (Abstract).

Milton Packer et al., The Effect of Carvedilol on Morbidity and Morality in Patients with Chronic Heart Failure, The New England Journal of Medicine, vol. 334, No. 21; May 23, 1996, pp. 1349–1355.

Olinescu R et al., Estimation of Oxidative Stress in Cardiovascular Diseases, Rom Journal Internal Medicine., 32(2); Apr.–Jun. 1994, pp. 129–136, (Abstract).

Pazzaglia PJ et al., Nimodipine Monotherapy and Carbamazephine Augmentation in Patients with Refractory Recurrent Affective Illness, Journal of Clinical Psychopharmacology, 18(5); Oct. 1998, pp. 404–413, (Abstract).

Pazzaglia PJ et al., Preliminary Controlled Trial of Nimodipine in Ultra–rapid Cycling Affective Dysregulation, Psychiatry Res. 49(3); Dec. 1993, pp. 257–272, (Abstract).

Richter A et al., Antidynamic Effects of L–type Ca2+ Channel Antangonists in a Hamster Model of Idiophatic Dystonia, Eur Journal Pharmacology, 300(3); Apr. 11, 1996, pp. 197–202, (Abstract).

Sachdev P et al., Intravenous Benztropine and Propranolol Challenges in Tardive Akathisia, Psychopharmacology (Berl), 113(1); 1993, pp. 119–122, (Abstract).

Sagara Y, Induction of Reactive Oxygen Species in Neurons by Haloperidol, J. Neurochem, 71(3); Sep. 1998, pp. 1002–1012, (Abstract).

Soares KV et al., The Treatment of Tardive Dyskinesia—A Systematic Review of Meta–Analysis, Schizophr Res, 39(1); Aug. 23, 1999, pp. 1–16, (Abstract).

Conrad Melton Swartz, Tardive Pyschopathology, Biological Psychiatry; 32; 1995, pp. 115–119.

Sze KH et al., Effect of Nimodipine on Memory After Cerebral Infarction, Acta Neurol Scand, 97(6); Jun. 1998, pp. 386–392, (Abstract).

David Tenero et al., Steady–State Pharmacokinetics of Carvedilol and Its Enantiomers in Patients with Congestive Heart Failure, Journal Clinical Pharmacology, 40; 2000, pp. 844–853.

Tetta C et al., An Overview of Haemodialysis and Oxident Stress, Blood Purif, 17(2–3); 1999, pp. 118–126 (Abstract).

Guochuan Tsai et al, Markers of Glutamatergic Neurotransmission and Oxidative Stress Associated with Tardive Dyskinesia, Am Journal Psychiatry, 155; Sep. 9, 1998, pp. 1207–1213.

Therdore Van Putten et al., Behavioral Toxicity of Antipsychotic Drugs, Journal Clinical Pharmacology, 48(9, suppl.); Sep. 1987, pp. 13–19.

Wils V, Respiratory Disorders Caused by Tardive Dyskinesia in Psychogeriatric Patients, Tijdschr Gerontol Geriatr, 23(3); Jun. 1992, pp. 109–113, (Abstract).

Yassa R et al., Prevalence of Tardive Dyskinesia in Affective Disorder Patients, Journal Clinical Psychiatry, 44(11); Nov. 1983, pp. 410–412, (Abstract).

Yue TL et al., Carvedilol Inhibits Activation of Stress–Activated Protein Kinase and Reduces Reperfusion Injury in Perfused Rabbit Heart, Eur Journal Pharmacology, 345(1); Mar. 12, 1998, pp. 61–65, (Abstract).

* cited by examiner

ADMINISTRATION OF CARVEDILOL TO MITIGATE TARDIVE MOVEMENT DISORDERS, PSYCHOSIS, MANIA, AND DEPRESSION

FIELD OF THE INVENTION

The present invention relates to medicine and to the administration of pharmaceuticals to relieve disorders of the brain and behavior. More particularly, the present invention relates to the treatment of movement disorders, including tardive dyskinesia, tardive dystonia and tardive akathisia.

BACKGROUND OF THE INVENTION

Tardive dyskinesia (TD) is an involuntary movement disorder which includes athetosis and chorea. It is usually caused by medication which blocks dopamine receptors, including many ordinary antipsychotic medications and antiemetic (antinausea) medications. Rarely is it caused by antidepressant medications. The "tardive" designation indicates that this disorder appears after persistent rather than acute exposure to such medication, typically at least six months in adults or three months in elderly patients. Athetosis is a slow writhing, and chorea is an undirected twitching movement. Commonly affected muscles include the tongue, the muscles around the mouth, the jaw, the neck, and the limbs, and the most visible TD movements include chewing, tongue protrusion, truncal and arm twisting, grimacing, and torticollis. TD is the most common of several tardive disorders of involuntary movement which occur in patients who take medication which blocks dopamine receptors.

Tardive dystonia tends to occur in patients who have TD, and it is characterized by long-sustained positions of muscle groups. Not only are the causes and circumstances of tardive dystonia indistinguishable from those of TD, but in medical practice the occurrence, manifestation, and treatment of tardive dystonia is not reliably distinguished from those of TD. Consequently, what refers to one refers as well to the other.

One group of medications notorious for causing TD is antipsychotic medications. Long-term use of antipsychotic medication which blocks dopamine receptors is a frequent part of the management of patients who have schizophrenia, schizoaffective disorder, psychotic mood disorders, postpartum psychosis, delusional disorder, Huntington's Disease, agitated dementias, psychoses consequent to chronic medical conditions, borderline personality disorder, porphyria, or Tourette's syndrome. Based on a 0.9% population prevalence for schizophrenia, 1–2% for psychotic mood disorders, 2% for agitated dementias, and 2–5% for the other conditions noted we expect that several million people in the USA have had persistent exposure to antipsychotic medications. The prevalence of TD increases with increasing exposure to such medication. Surveys report the prevalence of TD in patients with schizophrenia taking such medication as 32% after 5 years, 57% after 15 years, and 68% after 25 years (Glazer et al. 1993). In view of the increasing prevalence with greater drug exposure, the consensus among psychiatrists has long been that medication which blocks dopamine receptors is the most common cause of TD and tardive dystonia in patients they treat. Besides the duration of exposure to antipsychotic medication, advancing age increases the risk of TD (Yassa et al 1983; Hunt & Silverstone 1991); some elderly patients show persistent dyskinesia after a few weeks of an antipsychotic medication.

Antiemetic (antinausea) medications can similarly cause TD, particularly those which have antipsychotic properties or block dopamine receptors. Extended use of antidopamergic antiemetic medication can be used in the management of patients who suffer from nausea or vomiting. Nausea or vomiting can result from circumstances such as radiotherapy or chemotherapy for cancer, vertigo, pregnancy, Meniere's disease, peptic ulcer disease, panic disorder, irritable bowel syndrome or other gastrointestinal condition, or brain tumor. Based on the common nature of these conditions we expect that several million people in the USA have had persistent exposure to antiemetic medication that blocks dopamine receptors. Risk that a medication causes TD and other movement disorders is associated with its dopamine-blocking activity, rather than the reason for its administration, whether as an antiemetic, antipsychotic, or antianxiety agent; many dopamine-blocking drugs are usable for all these effects. Patients who receive these medications for antiemetic effect experience movement disorders including TD, tardive dystonia, and tardive akathisia just as those who receive these medications for antipsychotic effect do. More rarely, tardive dyskinesia is caused by other types of medications, particularly several types of antidepressants such as amoxapine, trazodone, nefazodone, tricyclics, and serotonin-reuptake inhibitors (SSRIs). Lithium has also been reported to exacerbate or cause TD.

TD is graceless and stigmatizing, and can disable a patient psychologically as well as physically. Many TD movements resemble expressions of rudeness, and suggest loss of ability to control one's self. These include tongue protrusion, lip puckering, facial grimacing, grunting, limb stiffening, and pelvic thrusting. These disfiguring movements are often obvious to even casual passers-by. TD can provoke repugnance, particularly in children and people with little education. This naturally leads people with TD to avoid exposure to people who are not knowledgeable friends, and to minimize their exposure to public places. This can cause substantial impairment of employability, household management, self-care, social function, and recreational function. In turn this can diminish earnings abilities, life satisfaction, and productivity, and cause unhappiness and anxiety symptoms.

In addition, long-term exposure to antipsychotic medication or dopamine-blocking antiemetic medication can produce adverse mental status changes together with or in place of TD. Analogous to the physical expressions of TD, such mental status changes are also graceless, stigmatizing, and debilitating. These mental status changes can include tardive psychosis, whose symptoms and signs are indistinguishable from schizophrenia, and other tardive psychopathology such as obsessions, compulsions, and depression (Chouinard et al 1978, Swartz 1995). Long-term exposure to dopamine-blocking medication can also produce tardive akathisia, which is a feeling of restlessness (Van Putten and Marder 1987). When akathisia is strong it is often accompanied by agitated movements, such as fidgeting, pacing, and leg-bouncing while sitting; such movements often vary considerably over the day (Sachdev and Loneragan 1993).

Akathisia differs from dyskinesia. Generally, patients do not pay attention to dyskinesia movements unless the movements are severe enough to substantially interfere with performance of a task. In contrast, akathisia generally impairs the patient's attention, and sometimes interrupts attention and concentration. The movements of dyskinesia generally do not resemble any movements made by people who are not ill. In contrast, the movements which are sometimes made in association with akathisia are the same as made by people who are normal but worried, frustrated, or disappointed.

Physical limitations caused by TD include dysphonia (Khan et al 1994), respiratory distress (Wils 1992), dysphagia (Hayashi et al. 1997), and deformation of bearing and posture (Maeda et al 1998). Because TD is often irreversible, the difficulties, limitations, and disfigurements it produces can be permanent. Indeed, permanent movement disorders develop in animals after long-term exposure to haloperidol and other dopamine-blocking medication, e.g., in Cebus monkeys (Casey 1996).

Trials of treatment for TD to date have proven no benefit (Soares & McGrath 1999), and there are no safe and effective treatments for TD (Najib 1999; Glazer 1999). "No treatment strategy . . . is successful in most patients" (Egan et al. 1997). The only method that will generally diminish the symptoms of TD is to stop the medication that caused the TD and hope for a decrease in symptoms with time. Unfortunately, before the symptoms decrease there is often at least a temporary increase which can be difficult to endure. Additionally, the symptoms for which the patient received the medication are likely to become worse, and there are often risks of violent injury or death to the patient or others.

A method that can temporarily diminish TD in some patients is to decrease dopaminergic neurotransmission, as by increasing a dopamine-receptor blocking medication or adding a drug that depletes body levels of dopamine, such as reserpine. Although these methods tend to diminish the symptoms, they tranquilize the patient and thereby impair psychological function and mental performance; further, these medications have adverse physical side-effects such as weight gain. Moreover, while these drugs decrease the observed signs of TD in the short term they continue the pathological process that underlies the TD, and they add to it; in the long term these drugs increase TD further.

Another method that can diminish TD in some patients is to administer an "atypical type" antipsychotic medication which does not block dopamine receptors as much, such as clozapine. Again, although this method may sometimes diminish the symptoms, it tranquilizes the patient and thereby impairs psychological function and mental performance; further, most of these medications have adverse physical side-effects. Although atypical antipsychotic medications might lessen the severity of TD in some cases, improvement is generally incomplete and new problems are exchanged for old. To illustrate, clozapine diminished TD in 43% of patients switched to it from another antipsychotic medication (Lieberman et al 1991), but clozapine's common adverse effects include weight gain, tiredness, and suppression of white blood cell production (agranulocytosis) with lethal risk from deficient functioning of the immune system. Because of this risk of death with clozapine, blood monitoring several times per month is required. In sum, there are no generally beneficial low-risk ways to mitigate TD.

The mechanism through which dopamine-blocking medication causes TD is not established, but the high incidence of irreversible changes in TD suggests there is a permanent deterioration or unrepaired injury (Miller & Chouinard 1993). The body reacts to dopamine receptor blockade by increasing the production of the neurotransmitter dopamine within the presynaptic nerve terminal and increasing the release of dopamine from the presynaptic nerve terminal into the synaptic cleft. However, dopamine is neurotoxic, and these increased levels of dopamine that develop in reaction to dopamine-blocking agents are likely to cause neuronal deterioration. It is our studied opinion that this neurotoxicity may be diminished by blockade of L-type calcium channels, antioxidant activity, or alpha- and beta-adrenergic receptor blockade, all of which are effects of carvedilol.

Further relative to TD as the result of a neurotoxic process, some studies observe that patients with TD tend to show increased levels of excitatory neurotoxic neurotransmitters and marginally higher levels of products of protein oxidation in the central nervous system (CNS) (Tsai et al. 1998). Haloperidol induces a several-fold increase of reactive oxygen species (Sagara, 1998), which is consistent with an excitatory neurotoxic process. Such observations suggest that an oxidative process might cause or exacerbate TD, and that an antioxidant agent might protect against TD or mitigate it. On the other hand, the dopamine-receptor blocking antipsychotic drugs chlorpromazine and trifluoperazine are potent antioxidants (Dalla Libera et al. 1998), but are also notorious for frequently causing TD and other adverse conditions. Moreover, elevated reactive oxygen is associated with several medical conditions, including heart failure (Olinescu et al. 1994) and chronic renal failure (Tetta et al. 1999), without causation of tardive dyskinesia. In sum, TD is not a specific result of oxygen stress, and no specific connection between the two has been proven.

Several psychiatrists reported giving the antioxidant vitamin E to patients with TD, but most studies found no significant improvement (Barak et al 1998). Vitamin E was speculated to possibly diminish TD in a minority, but benefit beyond random variation remains an unproven assertion supported by circumstantial evidence. The MAO-inhibitor pargyline reduced acute dystonias induced by antipsychotic medication in monkeys (Heintz and Casey 1987) and might have antioxidant effects. However, other effects by pargyline include increasing body levels of catecholamines and indoleamines, which themselves affect movement disorders and have antioxidant activities (Kang et al. 1998). The attribution of antidystonia effects to antioxidant activity requires that causation by the other effects of pargyline be disproven, but they were not. Likewise, correspondence between acute dystonias in monkeys and chronic choreoathetosis of TD in humans is speculative. Nevertheless, antioxidants have not been proven to show no benefit in TD; it was our impression that trial of a specially potent antioxidant might resolve this issue and show consistent effectiveness although ordinary antioxidants have failed to do so.

Several other medications have been said to diminish TD, but their effects on TD are controversial and were small at most. These medications include lithium and valproic acid. As an example of the controversy, some observers reported that lithium exacerbates TD or causes it.

The compound carvedilol has shown exceptionally potent in vitro antioxidant activity. Some of its metabolic products are also potent antioxidants. The administration of carvedilol to three psychiatric patients hospitalized under the care of the applicant was spurred by the prominent facial disfigurement these patients showed from TD, and by the recognition of carvedilol's antioxidant activity and its other pharmacological effects, as described below.

SUMMARY OF THE INVENTION

The absorption of carvedilol taken by mouth is typically rapid and complete. The average elimination half-life of carvedilol from the human body is about 8 hours. As with most pharmaceuticals, carvedilol is ordinarily removed from the body in a two-part process. First, the liver transforms it through one or more of the processes of hydroxylation, oxidation, sulfation, demethylation, and glucuronidation. Then, the kidneys transfer these transformed products into the urine. Some of the products of carvedilol transformation by the liver contribute to the beneficial effects of carvedilol administration. For example, the antioxidant activity of the carvedilol metabolite SB209995 has 50 to 100 times the potency of carvedilol and is 1000-fold more potent than vitamin E.

Carvedilol has several different effects on the body, including beta-1 and beta-2 adrenergic blockade, alpha-1 adrenergic blockade, antioxidant activity, L-type calcium channel blockade (Cheng et al. 1999), and inhibition of activation of stress-activated protein kinase (Yue et al 1998). All these should influence the central nervous system (CNS), excepting effects on beta-2 receptors, because they are not present in the CNS.

Among medications, carvedilol is particularly effective— and apparently uniquely so among modern medications—in decreasing the mortality of patients with longstanding heart failure (Packer et al. 1996; Cleland 1998) and increasing the heart's pump performance. The latter is measured by increasing cardiac ejection fraction (Cohn et al. 1997). Typical doses of carvedilol given to patients with congestive heart failure are 6.25 mg to 50 mg twice per day (Tenero et al. 2000). Even resistant patients, who failed to improve with the beta-blocker metoprolol, typically improved with carvedilol (Di Lenarda et al. 1999). Carvedilol's unique action led to the suggestion of synergism of antioxidant activity and beta-adrenergic blockade (Cleland 1998), a combination that also appears unique.

However, several other effects of carvedilol have beneficial actions and probably contribute to its therapeutic effects on TD and other movement disorders. These include L-type calcium channel blockade, inhibition of protein kinase, and alpha-1-adrenergic blockade. Accordingly, we reason that the beneficial effects of carvedilol might follow actions besides beta-blockade and antioxidant activity, and that a synergism might result from a combination of effects as noted but with or without these two particular effects. We consider the compound carvedilol to have therapeutic effects in tardive movement disorders by regarding that its beneficial effects on injured unrepaired heart similarly apply also to injured unrepaired brain, whether through antioxidant activity or another action or combination of actions. We reason that, similar to its beneficial effects on the heart, carvedilol should provide beneficial effects on the brain, to promote recovery, regeneration, and improved brain function for patients with tardive movement disorders. Examples of such tardive movement disorders include adverse consequences of medications that block dopamine receptors, such as tardive dyskinesia (TD), tardive dystonia, and the agitated movements that accompany tardive akathisia.

In its usually effective doses to treat TD, the side effects of carvedilol are nearly always non-existent or mild. This is a sharp contrast with mental dulling, personality changes, impairment of psychological performance, and weight gain from the antipsychotic medications that have been used to diminish TD.

The antipsychotic medications that acutely diminish TD also acutely diminish the symptoms of several psychiatric disorders, including: 1) psychoses including schizophrenia, 2) manic episodes (mania), 3) major depressive episodes (depression), especially when the depressive episodes include psychosis, and 4) agitation in patients who have dementia. The similarity between antipsychotic medications and carvedilol in the rapid and large mitigation of TD strongly, directly, and obviously suggests that they are similar in other pharmacological effects. Pharmacologically this similarity simply and obviously suggests that carvedilol acts to diminish the effects of high levels of dopaminergic activity. Clinically this similarity simply and obviously suggests that carvedilol diminishes the signs, symptoms, and severity of 1) psychoses including schizophrenia, 2) manic episodes (mania), 3) major depressive episodes (depression), especially when the depressive episodes include psychosis, and 4) agitation in patients who have dementia.

DETAILED DESCRIPTION OF THE INVENTION

The compound carvedilol has the chemical formula:

±-1-(carbazol-4-yloxy)-3-[[2-(o-methyoxyphenoxy)ethyl]amino]-2-propanol.

It exists in the form of optical isomers R- and S-carvedilol, and as mixtures of these isomers.

Because carvedilol's antioxidant activity is exceptionally potent, this activity has been speculated to be responsible for carvedilol's beneficial effects in diminishing heart failure and preventing recurrence of myocardial infarction. Carvedilol's antioxidant activity has been w observed in several ways. It protects against injury by oxygen free radicals to endothelial cells (the inner linings of blood vessels), vascular smooth muscle, and neurons, including during ischemia and during reperfusion after ischemia. Its antioxidant activities include inhibition of several actions: 1) direct toxic effects of oxygen radicals, 2) the ability of oxygen radicals to counteract nitrogen oxide-mediated vasodilation, 3) activation by oxygen radicals of genes associated with inflammation and 4) DNA fragmentation. Carvedilol also produces increases in body levels of endogenous antioxidants such as glutathione, which indicates replenishment of antioxidant defense mechanisms.

As outlined above, carvedilol has several other actions which are beneficial to injured brain. Among these is blockade of the L-type calcium channel current (Cheng et al. 1999), an effect rarely mentioned in publications about carvedilol. Antagonists of the L-type calcium channel are neuroprotective (McLeod et al 1998). From the opposite direction, activation of the calcium channel in neuronal tissues is a critical step towards neuronal injury and degeneration (Kobayashi & Mori 1998). Accordingly, we reason that L-type calcium channel blockade by carvedilol in neuronal tissues should shield the brain from injury and degeneration, and thereby allow it to recover and regenerate from previous injury. Blockade of the L-type calcium channel is the primary effect of the pharmaceutical nimodipine, and it is reasonable to expect that carvedilol has effects similar to nimodipine. So it is relevant to note that administration of nimodipine for 12 weeks improved memory in patients who had experienced stroke, when started 1 to 2 weeks after the stroke (Sze et al. 1998). Nimodipine improved memory, performance, and mood in a 12 week trial on elderly patients with dementia (Ban et al. 1990), and it diminished essential tremor in most cases (Biary et al 1995). Similarly, L-type calcium channels contribute to dystonias in several animal models, and nimodipine mitigated these dystonias (Richter & Loscher 1996; Campbell & Hess 1999). Nimodipine provided benefit to patients with major depressive disorder and bipolar mood disorder (Pazzaglia et al. 1998; 1993). Overall, its L-type calcium channel blockade activity provides another rationale for activity by carvedilol against neuronal injury and degeneration, and for its mitigation of neuropsychiatric disorders including movement disorders.

Blockade of alpha- and beta-adrenergic receptors might contribute to carvedilol's mitigation of tardive dyskinesia, but probably only in conjunction with carvedilol's other effects. Only long-term and not brief duration of beta-blockade by itself diminished TD (Karniol & Portela 1982; Schrodt et al. 1982); as described below, carvedilol had an extremely rapid onset of effectiveness against TD, so this rapidity is not attributable to beta-blockade alone. In an animal model of TD, one-day and two-week trials of the beta-blocker propranolol did not diminish orofacial movements caused by the antipsychotic dopamine-receptor blocker haloperidol (Takeuchi et al 1998). Blockade of alpha-1 adrenergic receptors produces dilation of arteries and arterioles, which tends to increase blood flow and thereby dilute and carry away locally high concentrations of toxic species, such as reactive oxygen, which are produced by injured brain tissue. This should diminish toxic self-injurious "positive-feedback" cycles, as can occur with neuronal releases of calcium and glutamate. In contrast to the lack of benefit from beta-blockers alone in tardive dyskinesia, beta-blockers diminish akathisia (Sachdev & Loneragan 1993). This effect is separate from a decrease in dyskinesia, just as akathisia is separate from dyskinesia. Nevertheless, carvedilol provides a unique action to diminish both tardive dyskinesia and tardive akathisia with a single pharmaceutical agent.

None of the pharmaceutical actions of carvedilol are specific to sexual function, sexual characteristics, or gender. Accordingly, carvedilol should have similar beneficial effects in both males and females.

In the present invention, carvedilol is orally administered to decrease, prevent, or diminish the progression of the movement disorders that can be caused by medication which blocks dopamine receptors. The movement disorders include tardive dyskinesia and tardive dystonia, and they also include the agitated movements that accompany tardive akathisia. It is reasonable to expect that these particular signs and symptoms represent particular similar pathological brain states regardless of the cause of those brain states, one of which is exposure to medication which blocks dopamine receptors. The beneficial effects of carvedilol on these mental signs and symptoms and on TD should be seen in patients regardless of diagnosis or apparent causative factors. Patients for whom these symptoms or signs are a source of substantial distress or impairment should experience diminution of these symptoms and signs from a suitable dose of carvedilol, with associated decreases in symptoms, complaints, or impairments. Such mental disorders include schizophrenia, schizoaffective disorder, schizophreniform disorder, mood disorders such as major depressive disorder and bipolar disorder, obsessive-compulsive disorder, delusional disorder, anxiety disorders, psychoses consequent to chronic medical conditions, and Tourette's syndrome.

The Effects of Carvedilol on Tardive Dyskinesia

EXAMPLES

Case #1:

This 47 year old Caucasian female was seen in the hospital. On examination she showed choreic (jerking) and athetotic (writhing) movements of the tongue, including repeated prominent protrusion of the tongue from the mouth. These movements were consistent with tardive dyskinesia. She also showed substantial agitation, as a sign of tardive akathisia. She mentioned having been told by several psychiatrists that she has tardive dyskinesia, and that she'd previously taken numerous different antipsychotic drugs, including risperidone, olanzapine, and clozapine. Clozapine is recognized as a drug that, because of dangerous side-effects, is reserved as the last resort after the failure of long courses and high doses of several other antipsychotic medications. On the third hospital day, a Friday (Nov. 13, 1998), the tongue protrusion movements continued unchanged. Carvedilol 6.25 mg once daily was then started. On 11/15 the carvedilol dose was increased to 6.25 mg twice daily. When next evaluated, at 9am on Monday 11/16, the tongue protrusions were absent. The absence of dyskinesia persisted despite the patient's repeated expressions of anxiety and anxious thoughts. With the lack of any faintness or bradycardia, the dose of carvedilol was increased to 6.25 mg in the morning and 12.5 mg at bedtime. Agitation then decreased, a sign of improvement in tardive akathisia. On the ninth hospital day carvedilol was discontinued. The patient was discharged on the 15th hospital day, without recurrence of any tongue protrusion, and without observable agitation.

Case #2:

This 37 year old Caucasian female seen in the hospital had been taking high doses of haloperidol for several years, including 30 mg/day orally and depot haloperidol decanoate intramuscularly 50 mg/week, to treat bipolar mood disorder and an anxiety disorder. Administration of haloperidol was discontinued three months prior to this hospitalization, so that the effects of depot haloperidol decanoate were nearly worn off. On examination she showed a prominent tongue protrusion every two minutes, felt to be a severe manifestation of tardive dyskinesia. She spontaneously complained that children in her neighborhood mocked her and called her a witch because of the tongue movements. She stated that she avoids leaving the house because of harassment by the children. She also showed the agitated movements that accompany tardive akathisia. On the first hospital day carvedilol 3.125 mg twice daily was started. On interview the next day no extensions of the tongue out of the mouth occurred, and she was discharged that day. She was rehospitalized 11 days later, and had not been taking carvedilol. Prominent tongue protrusions were seen every 2 to 3 minutes. Carvedilol was then restarted. Beginning on the next day tongue protrusions were no longer seen. The patient was discharged after one week; at the time of discharge there were no agitated movements consistent with tardive akathisia. The patient said that with the disappearance of these unwanted movements she felt calmer and happier overall, and her mood problems and anxiety symptoms were less. Carvedilol was continued for a month. During this time no tongue protrusions or agitated movements were seen, and the patient did not experience an episode of mood disorder; thus, it both diminished and prevented the progression of the symptoms of TD and tardive akathisia. The good clinical condition of the patient suggests that carvedilol also contributed to the prevention of recurrence of manic episodes and depressive episodes. Carvedilol was then discontinued and the symptoms of TD and tardive akathisia returned within a week.

Case #3:

This 64 year old Caucasian female was admitted to the hospital for the treatment of an anxiety disorder whose symptoms included insomnia, nightmares, unhappiness, suicidality, continual worry, and panic attacks. She had previously taken the antidepressants nortriptyline and fluoxetine, and was taking nefazodone 375 mg/day for one year. She was also taking the antihypertensive medication benazepril 40 mg/day, and the sleeping medication zaleplon 10 mg/day. On examination she showed prominent choreic tongue protrusion, athetotic chewing movements with an empty mouth, and pouting and puckering of the lips. On the Abnormal Involuntary Movement Scale (AIMS) she was rated with a score of 11. She then received carvedilol 3.125 mg twice daily. Twenty-four hours later, after two doses, chewing movements were gone, lip and tongue movements were in normal range, and the AIMS score fell to 6. Carvedilol was then discontinued and the symptoms returned just as they were prior to treatment.

Case #4:

This 53-year-old Caucasian male was in the hospital because of difficulty swallowing. This began about a year prior to hospitalization while taking haloperidol and lithium medications. Increasingly he would cough while eating or drinking. He had taken haloperidol and lithium for many years to treat bipolar manic-depressive illness. The swallowing difficulty worsened despite replacement of lithium and haloperidol with divalproex and olanzapine. In the hospital testing by the Speech Therapy Department found that when he tried to swallow he would aspirate fluid into his lungs. This aspiration put him at risk of aspiration pneumonia, which is disabling and can be life-threatening. For him to receive water and food a tube was surgically inserted between his stomach and the outside of his abdomen. On examination he showed prominent dystonia of the neck and head, with frequent abrupt obvious extension movements of the neck muscles of moderate degree. When he tried to drink water from a cup these movements obviously interfered with swallowing. He also showed mild dystonia of the eyebrows and forehead muscles, which were displaced upward. His tongue showed moderate dyskinesia; he could not hold it still. On the Abnormal Involuntary Movement SCALE (AIMS) he scored 13. He then received carvedilol 6.25 mg twice daily. Twenty-eight hours later, after three doses, his swallowing was rated by the Speech Therapy Department as 70% improved. The neck dystonia had decreased from moderate to mild, the facial dystonia had disappeared, the tongue dyskinesia had decreased from mild to marginal, and the AIMS score was 8.

All four cases indicate that carvedilol can treat the physical manifestations of TD. The first three cases indicate treatment of tardive akathisia. In the first two cases TD disappeared from one regular workday to the next, a weekday in one case and a weekend in the other case. In the third case, all observable abnormal movements disappeared in one day, and only a few slight similar movements that did not appear clearly abnormal remained. The movements associated with tardive akathisia observable in the first two cases also improved with carvedilol administration. Debilitating tardive dystonia decreased importantly with carvedilol administration in the fourth case. The stability of response and good mood observed in the second case indicates that carvedilol may act to prevent manic episodes, depressive episodes, and psychosis in patients with a history of these. The extreme rapidity and extent of response seen exceeds what can be attributed to carvedilol's antioxidant activity alone. Accordingly, much of the clinical benefit from carvedilol presumably derives from another action or a combination of actions, as outlined above.

References Cited

Ban T A, Morey L, Aguglia E, Azzarelli O, Balsano F, Marigliano V, Caglieris N, Sterlicchio M, Capurso A, Tomasi N A, et al. Nimodipine in the treatment of old age dementias. Prog Neuropsychopharmacol Biol Psychiatry 1990;14:525–51

Barak Y, Swartz M, Shamir E, Stein D, Weizman A. Vitamin E (alpha-tocopherol) in the treatment of tardive dyskinesia: a statistical meta-analysis. Ann Clin Psychiatry 1998;10:101–105.

Biary N, Bahou Y. Sofi M A, Thomas W, al Deeb S M. The effect of nimodipine on essential tremor. Neurology 1995;45:1523–5.

Campbell D B, Hess E J. L-type calcium channels contribute to the tottering mouse dystonic episodes. Mol Pharmacol 1999;55:23–31

Casey D E. Behavioral effects of sertindole, risperidone, clozapine and haloperidol in Cebus monkeys. Psychopharmacology (Berl) 1996;124:134–140.

Cheng J, Niwa R, Kamiya K, Toyama J, Kodama I. Carvedilol blocks the replarizing K+ currents and the L-type CA2+ curent in rabbit ventricular myocytes. Eur J Pharmacol 1999;376:189–201.

Chouinard G, Jones B D, Annable L: Neuroleptic-induced supersensitivity psychosis. Am J Psychiatry 1978; 135:1409–1410.

Cleland J G. Carvedilol for heart failure: more than just a beta-blocker. Br J Hosp Med 1998;58:493–497.

Cohn J N, Fowler M B, Bristow M R, Colucci W S, et al., for the U.S. Carvedilol Heart Failure Society Study Group. Safety and efficacy of carvedilol in severe heart failure. J Card Fail 1997;3:173–179.

Di Lenarda A, Sabbadini G, Salvatore L, Sinagra G, Mestroni L, Pinamonti B, Gregori D, Ciani F, Muzzi A, Klugmann S, Camerini F. Long-term effects of carvedilol in idiopathic dilated cardiomyopathy with persistent left ventricular dysfunction despite chronic metoprolol. The Heart-Muscle Disease Study Group. J Am Coll Cardiol 1999;33:1926–34

Egan M F, Apud J, Wyatt R J. Treatment of tardive dyskinesia. Schizophr Bull 1997;23:583–609

Glazer W M, Morgenstern H, Doucette J T. Predicting the long-term risk of tardive dyskinesia in outpatients maintained on neuroleptic medications. J Clin Psychiatry 1993;54:133–139.

Glazer W M. Review of incidence studies of tardive dyskinesia with typical antipsychotics. J Clin Psychiatry Audiograph Series, 1999;2:1–16.

Hayashi T, Nishikawa T, Koga I, Uchida Y, Yamawaki S. Life-threatening dysphagia following prolonged neuroleptic therapy. Clin Neuropharmacol 1997;20:77–81.

Heintz R, Casey D E. Pargyline reduces/prevents neuroleptic-induced acute dystonia in monkeys. Psychopharmacology (Berl) 1987;93:207–213.

Hunt N, Silverstone T. Tardive dyskinesia in bipolar affective disorder: a catchment area study. Int Clin Psychopharmacol 1991;6:45–50.

Kang M Y, Tsuchiya M, Packer L, Manabe M. In vitro study on antioxidant potential of various drugs used in the perioperative period. Acta Anaesthesiol Scand 1998;42:4–12.

Khan R, Jampala V C, Dong K, Vedak C S. Speech abnormalities in tardive dyskinesia. Am J Psychiatry 1994;151:760–762.

Kobayashi T, Mori Y. Ca2+ channel antagonists and neuroprotection from cerebral ischemia. Eur J Pharmacol 1998;363:1–15.

Lieberman J A, Saltz B L, Johns C A, Pollack S, Borenstein M, Kane J. The effects of clozapine on tardive dyskinesia. Br J Psychiatry 1991;158:503–10

Maeda K, Ohsaki T, Kuki K, Kin K, Ideka M, Matsumoto Y. Severe antecollis during anitpsychotics treatment: a report of three cases. Prog Neuropsychopharmacol Biol Psychiatry 1998;22:749–759.

McLeod J R, Shen M, Kim D J, Thayer S A. Neurotoxicity mediated by aberrant patterns of synaptic activity between rat hippocampal neurons in culture. J Neurophysiol 1998;80:2688–2698.

Miller R, Chouinard G. Loss of striatal cholinergic neurons as a basis for tardive and L-dopa-induced dyskinesias, neuroleptic-induced supersensitivity psychosis and refractory schizophrenia. Biol Psychiatry 1993;34:713–38

Najib J. Tardive Dyskinesia: A Review and Current Treatment Options. Am J Ther 1999;6:51–60

Packer M, Bristow M R, Cohn N J, et al., for the US Carvedilol Heart Failure Society Study Group. The effect of carvedilol on morbidity and mortality in patients with chronic heart failure. N Engl J Med 1996;334:1349–1355.

Olinescu R, Popovici D, Hertoghe J, Hulea S. Estimation of oxidative stress in cardiovascular diseases. Rom J Intern Med 1994;32:129–36

Pazzaglia P J, Post R M, Ketter T A, Callahan A M, Marangell L B, Frye M A, George M S, Kimbrell T A, Leverich G S, Cora-Locatelli G, Luckenbaugh D. Nimodipine monotherapy and carbamazepine augmentation in patients with refractory recurrent affective illness. J Clin Psychopharmacol 1998;18:404–13

Pazzaglia P J, Post R M, Ketter T A, George M S, Marangell L B. Preliminary controlled trial of nimodipine in ultra-rapid cycling affective dysregulation. Psychiatry Res 1993; 49:257–72

Richter A, Loscher W. Antidystonic effects of L-type Ca2+ channel antagonists in a hamster model of idiopathic dystonia. Eur J Pharmacol 1996;300:197–202

Sachdev P, Loneragan C. Intravenous benztropine and propranolol challenges in tardive akathisia. Psychopharmacology (Berl) 1993;113:119–122.

Sagara Y. Induction of reactive oxygen species in neurons by haloperidol. J Neurochem 1998;71:1002–1012.

Soares K V, McGrath J J. The treatment of tardive dyskinesia—a systematic review and meta-analysis. Schizophr Res 1999;39:1–16

Swartz C M. Tardive psychopathology. Neuropsychobiology 1995;32:115–119.

Sze K H, Sim T C, Wong E, Cheng S, Woo J. Effect of nimodipine on memory after cerebral infarction. Acta Neurol Scand 1998; 97:386–92

Tenero D, Boike S, Boyle D, Ilson B, Fesniak H F, Brozena S, Jorkasky D. Steady-state pharmacokinetics of carvedilol and its enantiomers in patients with congestive heart failure. J Clin Pharmacol 2000;40:844–853.

Tetta C, Biasioli S, Schiavon R, Inguaggiato P, David S, Panichi V, Wratten M L. An Overview of Haemodialysis and Oxidant Stress. Blood Purif 1999;17:118–126

Tsai G, Goff D C, Chang R W, Flood J, Baer L, Coyle J T. Markers of glutametergic neurotransmission and oxidative stress associated with tardive dyskinesia. Am J Psychiatry 1998;155:1207–1213.

Van Putten T, Marder S R. Behavioral toxicity of antipsychotic drugs. J Clin Psychiatry 1987; 49 (9, Suppl):13–19.

Wils V. Respiratory disorders caused by tardive dyskinesia in psychogeriatric patients. Tijdschr Gerontol Geriatr 1992;23:109–113.

Yassa R, Ghadirian A M, Schwartz G. Prevalence of tardive dyskinesia in affective disorder patients. J Clin Psychiatry 1983;44:410–412.

Yue T L, Ma X L, Gu J L, Ruffolo R R, Feuerstein G Z. Carvedilol inhibits activation of stress-activated protein kinase and reduces reperfusion injury in perfused rabbit heart. Eur J Pharmacol 1998;345:61–65.

What is claimed is:

1. A method of treating tardive dyskinesia, tardive dystonia, and tardive akathisia which arose from the administration to a patient of antipsychotic or antiemetic medication, consisting essentially of administering to the patient an effective amount of the compound carvedilol, or a pharmaceutically acceptable addition salt thereof, or a pharmaceutically acceptable optical isomer thereof, wherein the compound is administered orally in the amount of 3–50 mg one to four times per day.

2. A method of preventing the symptoms, signs and development of tardive dyskinesia, of tardive dystonia, and of tardive akathisia which follow the administration to a patient of antipsychotic medication, consisting essentially of administering to the patient an effective amount of the compound carvedilol, or a pharmaceutically acceptable addition salt there of, or a pharmaceutically acceptable optical isomer thereof, wherein the compound is administered orally in the amount of 3–50 mg one to four times per day.

3. A method of preventing the progression and further development of the symptoms and signs of tardive dyskinesia, of tardive dystonia, and of tardive akathisia which follow the administration of an antipsychotic medication to a patient, consisting essentially of administering to the patient an effective amount of the compound carvedilol, or a pharmaceutically acceptable addition salt thereof, or a pharmaceutically acceptable optical isomer thereof, wherein the compound is administered orally in the amount of 3–50 mg one to four times per day.

* * * * *